US005230328A

United States Patent [19]

Buchholtz et al.

[11] Patent Number: 5,230,328

[45] Date of Patent: Jul. 27, 1993

[54] ELECTROMAGNETIC ACOUSTIC PRESSURE PULSE SOURCE

[75] Inventors: Gerhard Buchholtz; Matthias Mahler, both of Erlangen, Fed. Rep. of Germany

[73] Assignee: Siemens Aktiengesellschaft, Munich, Fed. Rep. of Germany

[21] Appl. No.: 909,303

[22] Filed: Jul. 6, 1992

[30] Foreign Application Priority Data

Jul. 29, 1991 [DE] Fed. Rep. of Germany ....... 4125088

[51] Int. Cl.[5] ............................................. A61B 17/22

[52] U.S. Cl. ........................... 128/24 EL; 128/660.03

[58] Field of Search .......... 128/24 EL, 660.03, 419 S, 128/419 F; 600/13, 14; 367/175

[56] References Cited

U.S. PATENT DOCUMENTS 4,697,588 10/1987 Reichenberger .
4,782,821 11/1988 Reitter .
4,807,627 2/1989 Eisenmenger .................. 128/24 EL
4,901,709 2/1990 Rattner ........................... 128/24 EL
4,924,858 5/1990 Katona ........................... 128/24 EL

FOREIGN PATENT DOCUMENTS 0209053 7/1986 European Pat. Off. .
3312014 11/1985 Fed. Rep. of Germany .

*Primary Examiner*—Richard J. Apley
*Assistant Examiner*—Jeanne Mollo
*Attorney, Agent, or Firm*—Hill, Steadman & Simpson

[57] ABSTRACT

An electromagnetic acoustic pressure pulse source has a membrane with at least one electrically conductive region, the membrane being disposed for interacting on one side with an acoustic propagation medium, and having an opposite side facing a flat, spiral coil arrangement. The coil arrangement is driven with high-voltage pulses which cause the membrane to be rapidly repelled from the coil arrangement, thereby generating a pressure pulse in the acoustic propagation medium. The potential difference between the turns of the coil arrangement and the electrically conductive region of the membrane varies across the membrane, and the membrane is provided with a depression on the side thereof facing the coil arrangement in a region of high potential difference between the turns of the coil and the electrically conductive region of the membrane.

15 Claims, 2 Drawing Sheets

ELECTROMAGNETIC ACOUSTIC PRESSURE PULSE SOURCE

BACKGROUND OF THE INVENTION

1. Field of the Invention

The present invention is directed to an electromagnetic acoustic pressure pulse source, of the type having a membrane which is electrically conductive in at least one region, an acoustic propagation medium disposed on one side of the membrane, and a flat, spiral coil arrangement disposed on an opposite side of the membrane, for driving the membrane to cause the generation of a pressure pulse in the acoustic propagation medium.

2. Description of the Prior Art

Pressure pulse sources are used, for example, for medical purposes in the treatment of stone pathologies (lithotripsy), tumors and bone pathologies (osteorestoration). An electromagnetic shockwave generator is disclosed in European Application 0 259 559 wherein pressure pulses are generated by driving the membrane with a spiral coil arrangement having terminals connected to a high-voltage pulse generator which charges the coil with high-voltage pulses having an amplitude in the kilovolt range, for example, 20 kV. Such high-voltages can be generated, for example, by capacitor discharges. When the spiral coil arrangement is charged with such a high-voltage pulse, it generates a magnetic field extremely quickly. Simultaneously, a current is induced in the membrane, or at least in the electrically conductive region thereof, which is directed oppositely to the current flowing in the coil. The membrane current consequently produces an opposing magnetic field, causing the membrane to be rapidly moved away from the spiral coil arrangement. The pressure pulse initiated in the acoustic propagation medium, which is preferably a liquid such as water, is introduced in a suitable manner into the subject to be charged with the pressure pulses. As necessary, focusing of the pressure pulses may be undertaken before the pressure pulses reach the subject, for example by means of an acoustic lens.

In order to achieve a high efficiency of the energy conversion while avoiding voltage arcing between the spiral coil arrangement and the membrane (or the electrically conductive region thereof), which can reduce the useful life of the pressure pulse source, known pressure pulse sources provide a spacing between the turns of the spiral coil arrangement and the membrane which is greater in those regions of large potential differences between the turns of the spiral coil arrangement and the membrane, as compared to regions having a smaller potential difference. This is achieved in known structures by arranging the turns of the spiral coil on a seating surface consisting of an insulating material which is shaped so that the aforementioned spacing results between the turns of the spiral coil and the membrane. Thus even in the case of standard, planar membranes, a planar seating surface cannot be used. The presence of this uneven seating surface complicates both the manufacture of the seating surface and the winding of the spiral coil arrangement thereby resulting in substantial production-associated outlay and increased manufacturing time and costs.

SUMMARY OF THE INVENTION

It is an object of the present invention to provide an electrodynamic pressure pulse source of the type described above having a structure which provides the necessary spacing between the coil and the electrically conductive portion of the membrane, but which does so in a simple and economic manner.

The object is achieved in accordance with the principles of the present invention in an electromagnetic pressure pulse source having a membrane which is electrically conductive at least in regions thereof, having one side facing an acoustic propagation medium, and having an opposite side facing a flat, spiral coil arrangement for driving the membrane, and the membrane having at least one depression disposed in an electrically conductive region of the membrane on a side thereof facing the coil arrangement in a region having a large difference in electrical potential between the turns of the coil arrangement and the electrically conductive region of the membrane. Such a depression can be manufactured in a simple and economic manner in terms of production engineering in preferred embodiments of the invention wherein the depression is produced by an uncut deformation of the membrane. This means it is not necessary to cut into the membrane to produce the depression, however, a depression formed by cutting the membrane is within the scope of the invention. Deforming the membrane has the advantage that no measures whatsoever are necessary to achieve the necessary spacing which affect the spiral coil arrangement and the seating surface therefor. In the case of a membrane, which, except for the depression, is otherwise planar, and easily manufacturable, a planar seating surface can be employed, with the advantage that the spiral coil arrangement can be very easily wound on the seating surface. Because the high-voltage drops off along the turns of the spiral coil arrangement, the potential difference will vary (decrease) between the individual turns of the coil arrangement and the membrane along a side-elevation cross section of the coil and membrane. In order to avoid voltage arcing, and thus to assure a high useful life of the membrane, it is sufficient that the depression in the electrically conductive region of the membrane be limited so as to be coextensive with a few turns in that region exhibiting high potential differences relative to the membrane. When producing the depression by deforming the membrane without cutting or milling, the additional advantage of a strain-hardening of the electrically conductive region of the depression itself, and in a zone surrounding it, is achieved in the case of many materials, for example aluminum.

In a further embodiment of the invention, the depression contains insulating material. In comparison to a depression without insulating material, an extremely slight depth of the depression is sufficient when insulating material is used. A highly practical arrangement employs a piece of insulator foil contained in the depression and conforming in shape to the depression, the piece of insulator foil being glued to the membrane. Insulating material can thereby be introduced into the depression in this manner with an extremely low production outlay. Another simplification is achieved in an embodiment wherein the insulator foil is laminated to the membrane with an adhesive layer. For example, the insulator foil may be provided with an adhesive backing for attachment to the membrane. The insulating material preferably has such a thickness so that it does not project from the depression, and, if insulator foil is used, the insulator foil should not fall below the depth of the depression by more than 20% at any location. This assures that the membrane always presses flush against the flat, spiral coil when it is returned to its initial position with suitable measures, following the production of a pressure pulse, which is necessary in order to generate successive pressure pulses with coinciding acoustic parameters. This also insures that a high insulating effect will be achieved.

In another preferred embodiment of the invention, the spiral coil arrangement has an inner end disposed substantially in the center of the spiral coil, and an outer end situated in the region of an edge of the spiral coil arrangement. The depression is provided in a zone of the electrically conductive region which is adjacent the inner end of the coil arrangement. Investigations have shown that both the mechanical and thermal stressing of the membrane are at a maximum in its region disposed opposite the inner end of the spiral coil arrangement, given pressure pulse sources whose coil arrangement has an inner end disposed substantially in the center of the coil arrangement and an outer end disposed in the edge region of the coil arrangement. Providing the depression in that zone neighboring the inner end of the spiral coil arrangement therefore noticeably thermally relieves this zone because of the greater distance from the spiral coil arrangement. If the depression is manufactured in the form of an uncut and unmilled deformation of the membrane and if the electrically conductive region of the membrane consists of a strain-hardenable material, an increased strength of the electrically conductive region of the membrane is also achieved where the greatest mechanical stresses occur. If, in a further version of the invention, the electrically conductive region and the outer end of the spiral coil arrangement are at a common reference potential, as is usually the case in order to avoid voltage arcing between the inner end of the spiral coil arrangement which carries high voltage and the housing parts surrounding the pressure pulse source, the depression is preferably located in that region of the membrane having the greatest difference in potential compared to the spiral coil arrangement. In pressure pulse sources having a depression provided in the region of the inner end of the spiral coil arrangement, the depression is at least partially located in a region where the electromagnetic field is weak. The membrane, or the electrically conductive region thereof, tends to remain at rest at that location even when the membrane is charged with a high-voltage pulse. A depression which is produced by cold-working contributes to a stiffening in the central region of the membrane (or of the electrically conductive section) and thus ensures that that part of the membrane, or the electrically conductive section, which would remain at rest in the absence of a depression (due to the absence of repelling field forces) is now subject to excursion. The somewhat poorer electrical coupling in the center of the membrane, as a consequence of the locally greater spacing between the membrane (or the electrically conductive section) and the spiral coil arrangement is thus virtually completely compensated.

To facilitate filling of the depression with insulating material in the form of a piece of insulator foil, it is preferable that the depression has a constant depth. It is also possible, however, to allow the depth of the depression to decrease, preferably a continuous decrease toward its edge, so that the course of the depth of the depression changes in correspondence to the changing difference in potential between the electrically conductive region and the spiral coil arrangement. The depression, of course, has a smaller depth in regions having a smaller potential difference.

DESCRIPTION OF THE PREFERRED EMBODIMENTS

Figure 1:
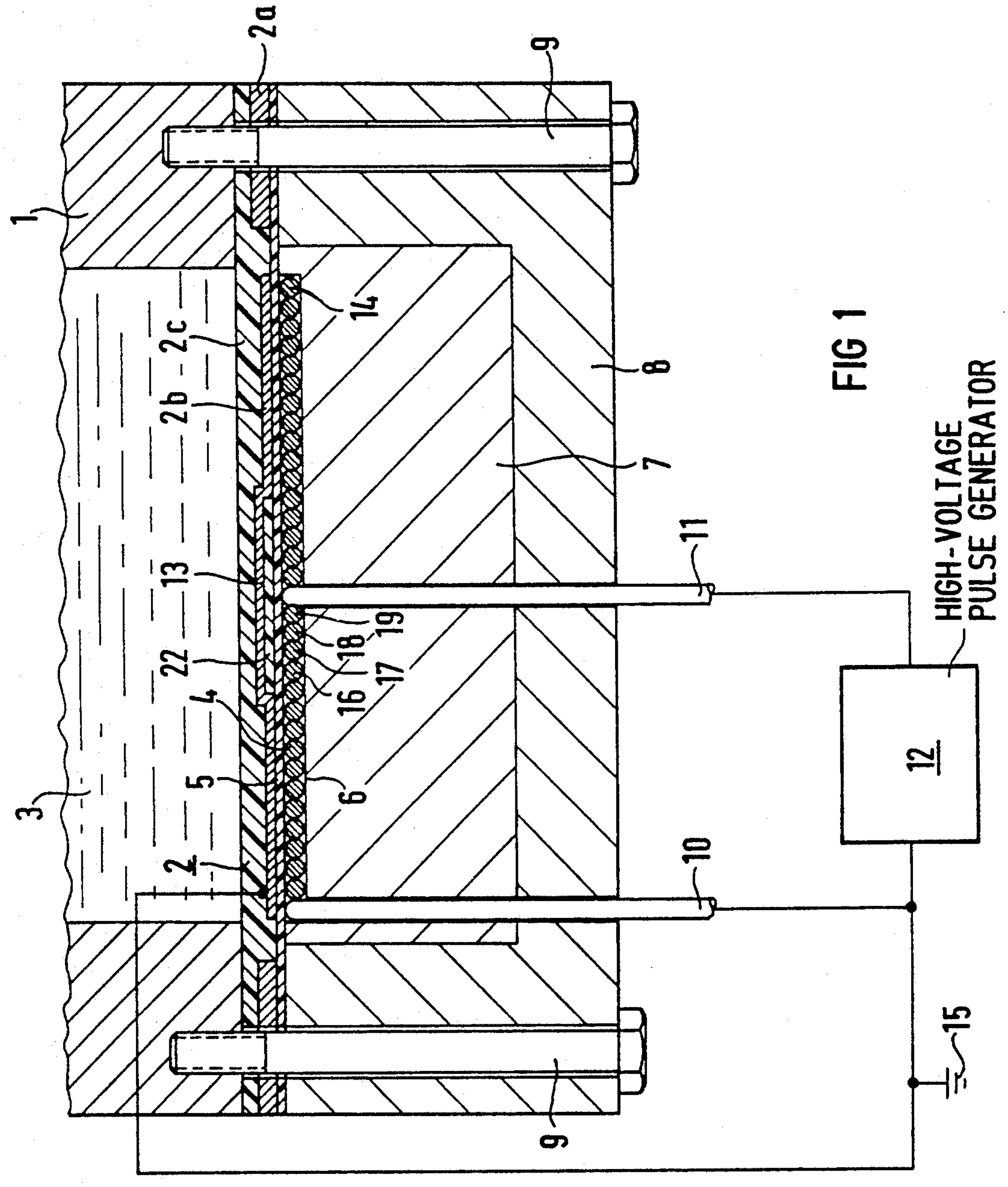
FIG. 1 is a longitudinal sectional view through a pressure pulse source constructed in accordance with the principles of the present invention.

The pressure pulse source shown in FIG. 1 has a housing 1 containing a volume 3 with a roughly circular cross section filled with a liquid, for example water, serving as an acoustic propagation medium. This volume 3 has one end closed by an approximately circular disc-shaped membrane 2. The membrane 2 is a composite part having an outer, metallic reinforcing ring *2a* having an annular shape, a circular disc-shaped part *2b* consisting of an electrically conductive material, for example aluminum, arranged concentrically inside the reinforcing ring *2a*, and a carrier *2c* which connects these two sections and consists of a cavitation-insensitive, elastically resilient material, for example rubber. The reinforcing ring *2a* and the part *2b* are embedded into that side of the carrier *2c* facing away from the liquid and are joined thereto with a material bond, for example by vulcanizing. The part *2b* represents the electrically conductive region of the membrane part, and since it is situated at the side of the carrier *2c* facing away from the liquid, it is protected by the carrier *2c* against deterioration due to corrosion and cavitation.

A flat coil arrangement in the form of an approximately circular disc-shaped coil 4 with spiral turns is provided at the opposite side of the membrane 2, i.e., the side facing away from the liquid. The flat coil 4 is arranged in the region of the electrically conductive part *2b* of the membrane 2. An insulating foil 5, preferably formed of Kapton ® is disposed between the membrane 2 and the flat coil 4. The turns of the flat coil 4 are arranged on a seating surface 6 of an insulator 7, which is received in a cap 8. The membrane 2, the insulating foil 5 and the cap 8 containing the insulator 7 with the coil 4 are secured to the housing 1 with screws 9.

For fixing the flat coil 4 against the seating surface 6 of the insulator 7, the space between the insulating foil 5 and the seating surface 6 of the insulator 7 is filled with an electrically insulating casting resin which, for clarity, is not separately shown.

The ends 10 and 11 of the flat coil 4 are connected to a schematically-indicated high-voltage pulse generator 12 via terminals which exit to the exterior of the pressure pulse generator through bores in the insulator 7 and the cap 8. The high-voltage pulse generator 12 charges the flat coil 4 with high-voltage pulses for generating pressure pulses. When the flat coil 4 is charged with a high-voltage pulse, the membrane 2 is rapidly repelled from the flat coil 4 as a consequence of the forces acting on the electrically conductive *2b*. This results in the formation of a pressure pulse in the liquid situated in the volume 3. This pressure pulse intensifies to form a shockwave during its path of travel through the liquid. As used herein, a shockwave means a pressure pulse having an extremely steep leading edge. Because the electrically conductive part 2b is resiliently joined to the reinforcing ring 2a via the carrier 2c, the excursion which occurs when a pressure pulse or shockwave is generated can be achieved without further measures.

It is important that the membrane 2 return to a defined initial position after each generation of a pressure pulse or shockwave, in order to insure that successive pressure pulses or shockwaves will have coincident characteristics. This initial position of the membrane 2 is flush against the flat coil 4, including the electrically conductive part 2b being flush against the flat coil 4. Return of the membrane 2 to this initial position after the generation of a pressure pulse or shockwave is achieved by charging either the space between the membrane 2 and the flat coil 4, or the space between the membrane 2 and the insulating foil 5, with a vacuum, as disclosed in European Application 0 188 750, or by placing the liquid situated in the volume 3 at a pressure which is elevated in comparison to the ambient pressure, as described in German OS 33 12 014.

As a consequence of the high-voltage across the flat coil 4 when charged with a high-voltage pulse, a potential difference gradient arises between the electrically conductive part 2b of the membrane and the individual turns of the flat coil 4. A potential difference gradient (as opposed to a uniform potential difference) arises because the potential difference varies over the membrane 2 and the coil 4, as viewed from the side as shown in FIG. 1.

In the pressure pulse source constructed in accordance with the principles of the present invention, the electrically conductive part 2b of the membrane 2 is provided with a depression 13 substantially coextensive with a region of the largest differences in potential between the turns of the flat coil 4 and the electrically conductive part 2b. There is thus an increased distance between the turns of the flat coil 4 and the electrically conductive part 2b in that region of largest potential differences. As schematically shown in FIG. 1, the outer end 10 connected to the outer turn 14 of the flat coil 4 and the electrically conductive part 2b of the membrane 2 are at substantially the same potential, namely grounded potential 15. There is thus a high different in potential between the inner turns of the flat coil 4 and the electrically conductive part 2b. The depression 13 is thus provided in the region of the innermost turns 16, 17, 18 and 19.

The depression 13 is disposed approximately centrally in the electrically conductive part 2b and has a circular shape and a constant depth. The depression 13 accepts a circular disc-shaped part 22 consisting of insulator foil, having a diameter corresponds to that of the depression 13. The part 22 is laminated with a plastic layer (not shown in FIG. 1) at its side facing the electrically conductive part 2b and is joined to the electrically conductive part 2b by gluing. The thickness of the part 22 is at most equal to the depth of the depression 13, and does not fall below the depth of the depression by more than 20%. Polyimide, for example, is suitable as the material for the insulator foil of the part 22.

The depression 13 is produced without cutting the electrically conductive part 2b by a pressing process using a cylindrical die with a diameter corresponding to that of the depression 13. Consequently, the electrically conductive part 2b has increased strength in the region of the depression 13 and the zone adjacent thereto due to strain-hardening.

As a consequence of the depression 13, the membrane 2 (or the electrically conductive part 2b thereof) has an improved electrical strength in the center of the membrane 2 where the electrical, mechanical and thermal stressing of the membrane is at a maximum and, in the case of production of the depression 13, without cutting the electrically conductive part 2b, the part 2b exhibits increased mechanical strength and a reduced thermal stressing. This results in an extended useful life of the membrane, and thus of the pressure pulse source.

Despite the increased distance between the flat coil 4 and the electrically conductive part 2b of the membrane 2 in the region of the depression 13, and thus a somewhat poorer electrical coupling between the flat coil 4 and the electrically conductive part 2b, the aforementioned measures do not result in a noteworthy reduction in the efficiency of the pressure pulse source in the above-identified regions, particularly since it is usually sufficient for the depression 13 to extend over a relatively small region of the electrically conductive part 2b.

Figure 2:
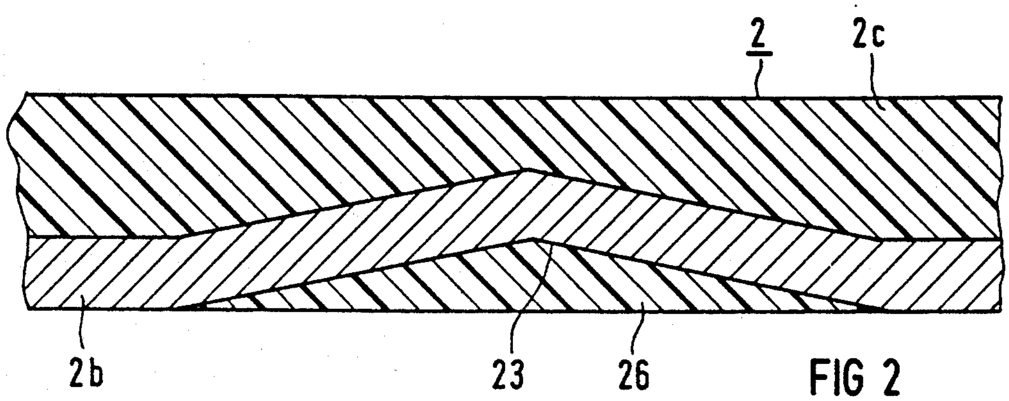
FIGS. 2 through 4 are respective enlarged views of different embodiments of the electrically conductive region of the membrane provided with a depression in a pressure pulse sources constructed in accordance with the principles of the present invention.
Figure 3:
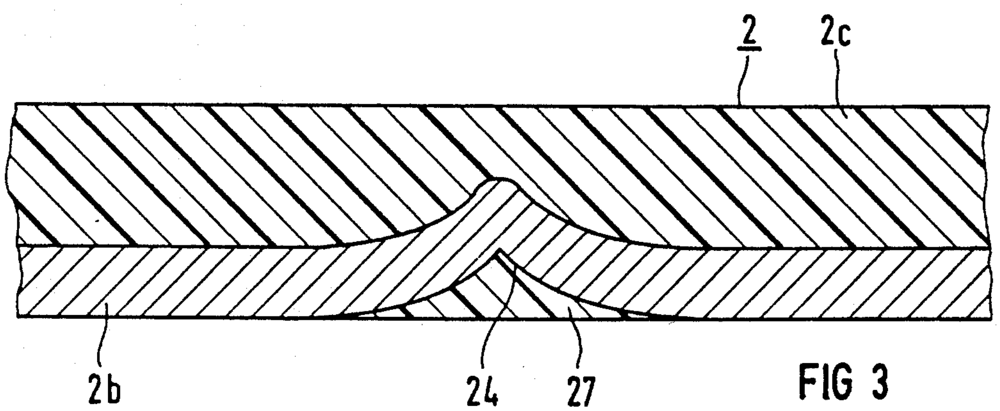
Figure 4:
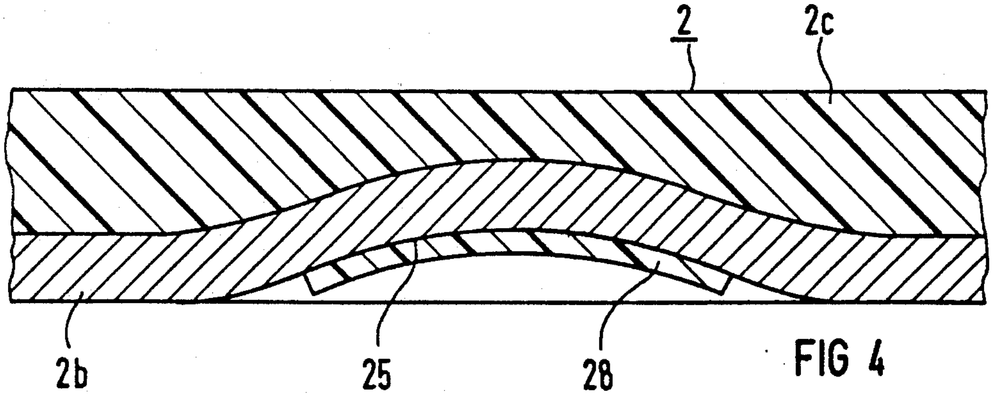

Further embodiments of different versions of membranes employable in the pressure pulse source of FIG. 1, are respectively shown enlarged in FIGS. 2 through 4. In these embodiments, the respective depressions 23, 24 and 25 of the electrically conductive part 2b do not have a constant depth. Instead, the depressions 23, 24 and 25, which are respectively filled with insulating material 26, 27 and 28, have a depth which continuously decreases toward the edge of the depressions 23, 24 and 25. The depth of the depressions 23, 24 and 25 thus accommodates the gradual decrease in the potential differences between the electrically conductive part 2b of the membrane 2 and the turns 19 through 16 of the flat coil 4. Whereas the decrease in the depth ensues linearly in the depression 23 in the embodiment of FIG. 2, the depth decrease ensues digressively in the depression 24 in the embodiment of FIG. 3 and ensues initially progressively and then digressively in the depression 25 in the embodiment of FIG. 4. The depressions 23, 24 and 25 are also produced without cutting the membrane 2 or the electrically conductive part 2b thereof, by means of correspondingly shaped dies. The thickness of the insulating material 26, 27 and 28 respectively located in the depressions 23, 24 and 25, and secured therein by gluing, is selected so that the insulating material does not project above the depression and, in the embodiments of FIGS. 2 and 3, does not have a thickness which anywhere falls below the depth of the respective depressions 23 and 24 by more than 20%. In FIGS. 2 and 3, the insulating material 26 and 27 is a shaped part. In the embodiment of FIG. 4, the insulating material 28 is a piece of self-adhesive insulator foil. The embodiment of FIG. 4 has advantages in view of its electrical strength, because sharp edges are avoided in the region of the depression 25, and thus in the region of high differences in potential.

The electrically conductive connection of the electrically conductive part 2b of the membrane 2 to ground potential 15 can be produced, for example, by grounding the reinforcing ring 2a and using a material for the carrier 2c such as a form of rubber which has been rendered conductive by the addition of graphite thereto.

The exemplary embodiments are directed to pressure pulse sources having a planar membrane 2. It is also possible, however, to employ the inventive concept disclosed herein in pressure pulse sources having differently shaped membranes, for example spherically shaped membranes.

If necessary, the electrically conductive region of the membrane may have a plurality of depressions. This may be expedient, for example, if the inner end of the flat coil 4 is at a positive potential, the outer end of the flat coil 4 is at a negative potential, and the membrane 2 or the electrically conductive part 2*b* thereof is at a potential therebetween. In this case, respective depressions would be provided in the region of the outer turns and in the region of the inner turns of the flat coil 4.

The membrane 2 need not, as described, necessarily be a composite part which is electrically conductive in only one region. A membrane may be used consisting entirely of an electrically conductive material. It is also possible to employ a membrane having a plurality of electrically conductive regions, with some or all of the those electrically conductive regions having a depression as necessary.

An essentially circular disc-shaped flat coil 4 having spiral turns is described in the exemplary embodiments. Flat coils having differently arranged turns may be used, however, as disclosed, for example, in European Application 0 209 053. Moreover, flat coil arrangements having a plurality of windings may also be employed, as also disclosed in European Application 0 209 053.

Although modifications and changes may be suggested by those skilled in the art, it is the intention of the inventors to embody within the patent warranted hereon all changes and modifications as reasonably and properly come within the scope of their contribution to the art.

We claim as our invention:

1. An electromagnetic pressure pulse source comprising:

a membrane disposed for interacting on one side with an acoustic propagation medium, said membrane having an electrically conductive region;

flat coil means disposed on an opposite side of said membrane for electromagnetically interacting with said electrically conductive region of said membrane to rapidly repel at least said electrically conductive region of said membrane from said coil means to generate a pressure pulse in said acoustic propagation medium, said coil means and said electrically conductive region of said membrane having a gradient of potential difference therebetween including a region of high-potential difference; and said electrically conductive region of said membrane having a depression in said opposite side of said membrane facing said coil means, said depression being relative to said coil means and being substantially coextensive with said region of high-potential difference for providing increased spacing between said electrically conductive region and said coil means.

2. An electromagnetic pressure pulse source as claimed in claim 1 wherein said depression is an uncut deformation of said membrane.

3. An electromagnetic pressure pulse source as claimed in claim 1 further comprising:

electrically insulating material contained in said depression.

4. An electromagnetic pressure pulse source as claimed in claim 3 wherein said insulating material has a shape conforming to the shape of said depression.

5. An electromagnetic pressure pulse source as claimed in claim 3 wherein said insulating material is a piece of insulator foil glued to said membrane.

6. An electromagnetic pressure pulse source as claimed in claim 5 wherein said insulator foil is glued to said membrane by an adhesive layer laminated to said insulator foil.

7. An electromagnetic pressure pulse source as claimed in claim 3 wherein said insulating material has a thickness so that said insulating material does not project from said depression.

8. An electromagnetic pressure pulse source as claimed in claim 7 wherein said insulating material has a thickness which does not fall below the depth of said depression by more than 20%.

9. An electromagnetic pressure pulse source as claimed in claim 1 wherein said coil means includes a spiral coil having an inner end disposed substantially at a center of said coil means and said membrane and an outer end disposed at an edge region of said coil means and said membrane, and wherein said depression is disposed in a zone of said electrically conductive region adjacent said inner end of said spiral coil.

10. An electromagnetic pressure pulse source as claimed in claim 9 wherein said electrically conductive region and said outer end of said spiral coil are at a common electrical potential.

11. An electromagnetic pressure pulse source as claimed in claim 1 wherein said depression has a constant depth.

12. An electromagnetic pressure pulse source as claimed in claim 1 wherein said depression has a varying depth.

13. An electromagnetic pressure pulse source as claimed in claim 1 wherein said depression has a center and an edge, and wherein said depression has a depth which continuously decreases from said center toward said edge.

14. An electromagnetic pressure pulse source as claimed in claim 1 wherein said depression has a varying depth which changes in accordance with said potential difference gradient.

15. An electromagnetic pressure pulse source as claimed in claim 1 wherein said depression has no sharp edges.

* * * * *